(12) United States Patent
Nelson et al.

(10) Patent No.: US 7,289,195 B1
(45) Date of Patent: Oct. 30, 2007

(54) SYSTEM AND METHOD FOR PASSIVELY ASCERTAINING A RELATIVE DIRECTION OF CHANGE IN DISTANCE BETWEEN AN ELECTROMAGNETIC-ENERGY EMITTER AND A SPECTRAL SENSOR

(75) Inventors: Richard J. Nelson, Brookline, NH (US); James E. Murguia, Hollis, NH (US)

(73) Assignee: Solid State Scientific Corporation, Hollis, NH (US)

( * ) Notice: Subject to any disclaimer, the term of this patent is extended or adjusted under 35 U.S.C. 154(b) by 238 days.

(21) Appl. No.: 11/270,969

(22) Filed: Nov. 12, 2005

Related U.S. Application Data

(60) Provisional application No. 60/627,654, filed on Nov. 13, 2004.

(51) Int. Cl.
G01C 3/08 (2006.01)
G01C 1/00 (2006.01)
G01N 21/00 (2006.01)

(52) U.S. Cl. .............................. 356/4.07; 356/139.04; 356/432

(58) Field of Classification Search ............... 356/4.01, 356/4.07, 5.01, 139.04, 337, 342, 432
See application file for complete search history.

(56) References Cited

U.S. PATENT DOCUMENTS 6,594,000 B2 * 7/2003 Green et al. ............... 356/5.01
6,995,846 B2 * 2/2006 Kalayeh et al. ............. 356/437
2002/0180951 A1 * 12/2002 Benz et al. ................ 356/5.01
2004/0130702 A1 * 7/2004 Jupp et al. ................. 356/5.01
2007/0109528 A1 * 5/2007 Caldwell et al. .............. 356/28

FOREIGN PATENT DOCUMENTS

EP 489546 A2 * 6/1992

* cited by examiner

*Primary Examiner*—Isam Alsomiri
(74) *Attorney, Agent, or Firm*—Louis J. Franco; Law Office of Louis J. Franco

(57) ABSTRACT

A system and method for determining whether the distance between an electromagnetic-energy emitting source and a predetermined location increased, decreased or remained constant between first and second times relies upon the selection of first and second energy bands whose average wavelengths are disparately absorbed as a function of transmission distance. Energy values corresponding to the intensity of detectable energy within each of the first and second sub-ranges at each of the first and second times are assigned. First and second ratios comparatively indicative of the intensity of energy detected, as represented by the assigned relative-energy values, within the first and second sub-ranges at each of the first and second times are computed and, based on a ratio-comparative analysis of the first and second ratios, a determination as to a direction of change in transmission distance is rendered by reference to modeled data associating, directly or indirectly, expected ratio-comparative relationships with an increase, decrease and lack of change in distance.

17 Claims, 6 Drawing Sheets

Partial data included in atmospheric-absorption-profile data set 235

SYSTEM AND METHOD FOR PASSIVELY ASCERTAINING A RELATIVE DIRECTION OF CHANGE IN DISTANCE BETWEEN AN ELECTROMAGNETIC-ENERGY EMITTER AND A SPECTRAL SENSOR

PROVISIONAL PRIORITY CLAIM

Priority based on Provisional Application Ser. No. 60/627,654, filed Nov. 13, 2004, and entitled "SYSTEM AND METHOD FOR PASSIVELY ASCERTAINING A RELATIVE DIRECTION OF CHANGE IN DISTANCE BETWEEN AN ELECTROMAGNETIC-ENERGY EMITTER AND A SPECTRAL SENSOR" is claimed. The content of the aforementioned provisional application is incorporated by reference herein in its entirety.

BACKGROUND

1. Field

Implementations of the present invention relate generally to the passive detection of relative motion between a spectral imager and an electromagnetic-energy emitting source (i.e., an object or event) within a predetermined atmosphere exhibiting an atmospheric electromagnetic-absorption profile and, more particularly, to missile-threat warning systems. Each of various implementations further involves a method and associated apparatus for capturing and analyzing the spectral signature of the energy-emitting source and, based on an algorithmic analysis of the spectral signature at different times, rendering a determination as to whether distance between the spectral sensor and the object or event of interest has (i) increased, (ii) decreased or (iii) remained constant over a specified time interval.

2. Brief Description of an Illustrative Environment and Related Art

Passive threat warning systems detect potential missile threats to aircraft and other assets by sensing emitted energy in the ultraviolet, visible, and/or infrared bands emitted from the suspected threat. These systems rely on spectral sensors and algorithms to discern actual threats from background clutter, for example. At present, infrared sensor technology as applied to a missile threat warning application implements a system wherein the energy emitted in one narrow band, or color, in the range of approximately 4.4 μm to 4.8 μm is compared to the energy emitted in another narrow band in the range of approximately 3.9 μm to 4.1 μm. Discernment between, for example, a so-called "sun glint" and an earth-bound "hot object" or "hot event" such as a fire, a missile burn or a flamethrower is based upon the knowledge that the detectable energy associated with direct or reflected sunlight is markedly more intense in the 3.9 μm to 4.1 μm range than in the 4.4 μm to 4.8 μm range, while the emission spectrum of an earthbound hot event is generally more intense in the 4.4 μm to 4.8 μm range than in the 3.9 μm to 4.1 μm range. Although such a "two-color sensor" facilitates the elimination from consideration as threats certain types of clutter sources (e.g., sun glints), current systems are generally incapable of further discerning whether an event not eliminated as clutter under the initial two-color regime presents an actual threat (e.g., whether the source of the emitted energy is closing in or moving away from the sensor).

Accordingly, there exists a need for a method and associated apparatus adapted for the passive detection of relative motion between a spectral imager and an electromagnetic-energy emitting source (i.e., an object or event) within a predetermined atmosphere.

SUMMARY

Implementations of various methods of determining the relative direction of changes in distance between an electromagnetic-energy emitting source and a predetermined location (e.g., a spectral sensor) rely on knowledge of certain characteristics generally exhibited by the atmosphere in which a particular implementation is intended for use. For instance, earth's atmosphere exhibits certain general characteristics of which various embodiments make use, including an atmospheric-electromagnetic-energy absorption profile. Although this profile may vary, even in earth's atmosphere, with temperature, humidity, pressure and particulate and pollution content, for example, these variables, in various implementations, are either factored in real time in a variant system or incorporated in an invariant system pre-determined to be applicable to a broad range of practical conditions and circumstances. Although implementations as a whole are broadly applicable to a wide variety of uses, certain illustrative implementations are applicable to threat warning systems incorporated in military assets such as aircraft, ships, ground vehicles and immobile shelters (e.g., buildings).

An illustrative implementation generally includes providing reference-profile data indicative of an electromagnetic-absorption profile associated with a model atmosphere and including indications as to the absorption behavior, within the model atmosphere, of each wavelength of a selected set of wavelengths as a function of transmission distance. A wavelength set within which to measure the relative intensity of detectable energy emitted from the emitting source is selected such that the selected wavelength set includes wavelengths for which absorption behavior as a function of transmission distance is represented in the reference-profile data. Selected from within the wavelength set are first and second energy sub-ranges such that (i) the first energy sub-range includes wavelengths whose average length is shorter than the average length of the wavelengths included in the second energy sub-range, (ii) the average wavelength within the first energy sub-range and the average wavelength within the second energy sub-range are disparately absorbed as a function of transmission distance in the predetermined atmosphere and (iii) each of the first and second sub-ranges includes at least one wavelength for which absorption behavior as a function of transmission distance is represented in the reference-profile data. The relative intensity of detectable energy emitted from the emitting source within each of the first and second energy sub-ranges is measured from the predetermined location at each of first and second times and two relative-energy values are assigned to (i.e., associated with) each of the first and second sub-ranges, each relative-energy value associated with one of the first and second sub-ranges corresponding to the intensity of energy detected in that sub-range at one of the first and second times. Each relative-energy value is typically representative of the average energy intensity registered, at one of the first and second times, in the sub-range with which it is associated. It is to be understood that the "predetermined location" is not necessarily stationary in 3-dimensional space; in many implementations, for example, the predetermined location is a spectral sensor carried by a moving vehicle such as an aircraft.

First and second ratios comparatively indicative of the intensity of energy detected, as represented by the assigned relative-energy values, within the first and second sub-ranges at each of the first and second times are computed. Based on a comparison between the first and second ratios, and reference to the reference-profile data, a determination is rendered as to whether the distance between the electromagnetic-energy emitting source and the predetermined location one of (a) decreased, (b) increased and (c) remained constant in the time elapsed between the first and second times. The electromagnetic-absorption profile associated with a model atmosphere, and represented by the reference-profile data, provides interpretive guidance by associating expected ratio-comparative relationships between the first and second ratios with increases, decreases and lack of change in distance between the emitting source and the predetermined location. Accordingly, various implementations further comprise establishing, in association with the reference-profile data and the selected first and second energy sub-ranges, a determinations set and ratio-comparative relationships set. A determinations set includes at least one of (a) a determination that the distance between the electromagnetic-energy emitting source and the predetermined location increased, (b) a determination that the distance between the electromagnetic-energy emitting source and the predetermined location remained unchanged and (c) a determination that the distance between the electromagnetic-energy emitting source and the predetermined location decreased. A ratio-comparative relationships set includes at least one of (a) an indication that the first ratio is greater in magnitude than the second ratio, (b) an indication that the first ratio is equal in magnitude to the second ratio and (c) an indication that the first ratio is lesser in magnitude than the second ratio. Determinations from the determinations set are correlated with indications from the ratio-comparative relationships set. For instance, (i) the determination that the distance between the electromagnetic-energy emitting source and the predetermined location remained unchanged is correlated to the indication that the first ratio is equal in magnitude to the second ratio; (ii) the determination that the distance between the electromagnetic-energy emitting source and the predetermined location increased is correlated with one of (a) the indication that the first ratio is greater in magnitude than the second ratio and (b) the indication that the first ratio is lesser in magnitude than the second ratio; and (iii) the determination that the distance between the electromagnetic-energy emitting source and the predetermined location decreased is correlated with the other of (a) the indication that the first ratio is greater in magnitude than the second ratio and (b) the indication that the first ratio is lesser in magnitude than the second ratio.

In order to render the method adaptable for reliable implementation under a variety of atmospheric conditions, the reference-profile data of alternative implementations include data indicative of plural disparate electromagnetic-absorption profiles, each of which profiles is associated with a model atmosphere and includes indications as to the absorption behavior, within the model atmosphere with which that profile is associated, of each wavelength of a selected set of wavelengths as a function of transmission distance. In such implementations, each profile is formulated on the basis of an assigned set of values for each atmospheric condition of a selected set of atmospheric conditions. A representative set of atmospheric conditions includes at least one of (i) temperature, (ii) humidity, (iii) suspended-particulate content, (iv) pressure and (v) altitude. An illustrative implementation that facilities the factoring of one or more of the atmospheric conditions further comprises steps of (a) measuring a value of at least one atmospheric condition within the pre-determined atmosphere within which a determination as to change in distance between the emitting source and the predetermined location is to be rendered and (b) selecting from the reference-profile data, as an analytical reference, the electromagnetic-absorption profile formulated on the basis of assigned set values corresponding most closely, relative to other profiles within the reference-profile data, to the at least one measured atmospheric-condition as a basis for rendering a determination as to whether the distance between the electromagnetic-energy emitting source and the predetermined location one of (a) decreased, (b) increased and (c) remained constant in the time elapsed between the first and second times based on a comparison between the first and second ratios.

Although a process in accordance with the preceding can, in general, be implemented using energy sub-ranges from anywhere on the electromagnetic spectrum, so long as the absorption characteristics associated with the sub-ranges are sufficiently disparate, as a function of transmission distance, to yield meaningful information, regions of the electromagnetic spectrum in the vicinity of so-called "dark regions" or "dark lines" exhibit absorption profiles that are relatively sharply-sloped and reliably disparate as a function of wavelength over a relatively wide range of wavelengths. Hence, selecting sub-ranges in the vicinity of a dark region is advantageous to various implementations. "Dark regions" or "dark lines" are more completely described in subsequent paragraphs associated with methods implemented by a programmed data-processing system (e.g., a computer), but those descriptions apply equally to more general implementations, irrespective of the extent, if any, to which they are executed with the aid of a computer. It is sufficient to note at present that, in various alternative implementations, a dark line represents a reference wavelength for which optical transmission within the predetermined atmosphere is minimized relative to other wavelengths within the selected wavelength range. In other implementations, first and second energy sub-ranges are selected with reference to a reference wavelength, but the reference wavelength is not itself included in the selected wavelength range.

In various implementations in which the wavelength range is selected so as to include a reference wavelength, or at least with reference to a reference wavelength, the reference wavelength functions as a delineation between a short-side wavelength set including wavelengths within the selected wavelength range that are shorter than the reference wavelength and a long-side wavelength set including wavelengths within the selected wavelength range that are longer than the reference wavelength. Accordingly, some versions include a step of selecting, within at least one of the short-side wavelength set and the long-side wavelength set, first and second energy sub-ranges from the same one of the first and second wavelength sets such that (i) the first energy sub-range includes wavelengths whose average length is shorter than the average length of the wavelengths included in the second energy sub-range and (ii) the average wavelength within the first energy sub-range and the average wavelength within the second energy sub-range are disparately absorbed as a function of transmission distance in the predetermined atmosphere. In various versions, energy sub-ranges within both of the short-side wavelength set and the long-side wavelength set are selected for comparative analysis as a matter of course and then a decision is rendered based on the combined results of the ratio comparisons performed in association with either side of the reference wavelength. In another set of implementations, one of the long-side and short-side wavelength sets is selected for initial ratio-comparative analysis and, depending on the results of the initial ratio comparison, a similar analysis is performed for sub-ranges within the other of the short-side and long-side wavelengths to "confirm" or "check" the result of the initial analysis. For example, a second ratio-comparative analysis may be performed for wavelengths on the opposite side of the reference wavelength when, for example, the initial ratio comparison indicates that distance did not change between the first and second times or when the first result otherwise does not exceed a predetermined confidence threshold. An implementation facilitating ratio-comparative analysis for energy sub-ranges on either side of a reference wavelength may also facilitate reliability over a longer range (i.e., transmission distance between the emitting source and the predetermined location). For instance, there are certain candidate-reference dark lines within a typical atmospheric-absorption spectrum for which use of long-side wavelengths produces more accurate results for ranges of, for example, 1 to 5 km, with the accuracy of the rendered determinations falling off sharply with greater distances. On the other hand, however, use of short-side wavelengths may produce superior results for longer transmission distances of, for example, 5 to 15 km. Accordingly, the ability of an illustrative implementation to produce acceptable results over a 15 km range may require that implementation's capacity to perform ratio-comparative analyses on either of the short-side and long-side wavelength sets. In any event, the first and second energy sub-ranges associated with any particular ratio-comparative analysis are typically selected from the same one of the short-side wavelength set and the long-side wavelength set and, for example, the energy values associated with an energy sub-range from the long-side wavelength set are not compared directly to the energy values associated with an energy sub-range from the short-side wavelength set in any single iteration of the method.

Various alternative methods include automated implementation and comprise providing a data processing system including a central processor and at least one memory device communicatively linked to the processor. A spectral sensor array adapted to detect wavelengths over a predetermined range of electromagnetic wavelengths is provided and communicatively linked to the data processing system. The wavelength range is selected so as to include a reference wavelength for which optical transmission within a predetermined atmosphere for which the sensor is adapted is minimized (i.e., at a minimum) relative to other wavelengths within the predetermined wavelength range. For example, it is well-known in the relevant arts that earth's atmosphere exhibits pronounced energy absorption (i.e., "dark lines") in the vicinities of 1.8 μm and 4.27 μm due to the presence in the atmosphere of, respectively, water ($H_2O$) and carbon dioxide ($CO_2$). Although the sensitivity of the spectral sensor can be selected so as to include either or both of the aforementioned "dark lines" along the absorption spectrum of earth's atmosphere, or any other dark line or dark band, for that matter, a wavelength range inclusive of 4.27 μm has been determined to be particularly useful in previous threat-warning applications and to particular implementations of the present invention. Accordingly, while it is to be understood that versions emphasizing regions of the absorption spectrum around alternative dark lines or dark bands within a given atmosphere are within the scope and contemplation of the invention as expressed in the appended claims, the discussion of particular illustrative implementations focuses on the carbon dioxide absorption band of earth's atmosphere (hereinafter, "the atmosphere") that is manifest in the vicinity of 4.27 μm.

The reference wavelength, in various versions, functions as an analytical delineation between a short-side wavelength set that includes wavelengths with the predetermined wavelength range that are shorter than the reference wavelength and a long-side wavelength set that includes wavelengths within the predetermined wavelength range that are longer than the reference wavelength. In alternative embodiments, wavelengths in only one of the short-side wavelength set and the long-side wavelength set are analytically significant.

Regardless of whether a particular implementation is adapted for ratio-comparative analysis of wavelengths in both or only one of the short-side and long-side wavelengths sets, methods include registering first and second spectral signatures of the electromagnetic-energy emitting source at, respectively, first and second times and storing in computer memory first and second data sets indicative of the first and second spectral signatures. A spectral analysis algorithm is executed which algorithm consults the first and second data sets and, within either or both of the short-side and long-side wavelength sets, operates on data representative of first and second energy sub-ranges selected such that the first energy sub-range includes wavelengths having an average length that is shorter than the average length of the wavelengths included in the second energy sub-range. In various implementations, first and second consecutive sub-ranges of one or each of the short-side and long-side wavelength ranges are selected for algorithmic analysis. For instance, on the long side of 4.27 μm, the ranges from 4.50 μm to 4.65 μm and 4.66 μm to 4.80 μm are first and second consecutive sub-ranges representing, in combination, a contiguous region of a long-side wavelength range with respect to the reference wavelength of 4.27 μm. It is to be understood, however, that overlapping first and second sub-ranges representing a contiguous region of the wavelength range, as well as first and second non-consecutive sub-ranges not representing a contiguous region, may be selected. Typically, however, the wavelength sub-ranges are best selected such that their average wavelengths are disparate.

Based on the registered first and second spectral signatures, the spectral analysis algorithm assigns a relative-energy value to each of the first and second sub-ranges within a wavelength set (i.e., the short-side or long-side wavelength set) indicative of the intensity of energy (e.g., average intensity) registered over the sub-range at each of the first and second times. With the aforementioned values assigned, the algorithm computes first and second ratios reflective of, respectively, the relative-energy values of the first and second sub-ranges within the wavelength set at each of the first and second times. Based on a comparison between the first and second ratios, the spectral analysis algorithm renders a determination as to whether the distance between the electromagnetic-energy emitting source and the spectral sensor one of (a) decreased, (b) increased and (c) remained constant in the time elapsed between the first and second times.

Implementations rely on the energy absorption characteristics of the atmosphere and, more particularly, on the fact that an atmospheric electromagnetic-absorption profile is dependent on wavelength as well as distance from the emitting source. That is, various wavelengths within the absorption spectrum of a particular atmosphere are disproportionately absorbed as a function of transmission distance. Accordingly, with reference to the known, expected or attributed absorption profile of a particular atmosphere, various implementations detect motion of an emitting source relative to a spectral sensor by analyzing ratios of measured energy in two sub-ranges of wavelengths, as previously described, from the same side of the reference wavelength, wherein, for example, the average wavelength within the first energy sub-range and the average wavelength within the second energy sub-range are disparately (e.g., disproportionately) absorbed as a function of transmission distance in the predetermined atmosphere. A comparison of the first and second ratios at first and second times enables a determination as to distance change. However, whether the second ratio's being greater than the first ratio indicates a decrease or increase in distance may depend on such factors as the sub-ranges chosen and, even when the two sub-ranges are not varied, variables in the atmosphere in which the measurements are taken (e.g., temperature, particulate content, humidity, pressure and altitude). Accordingly, as alluded to previously, one set of embodiments includes versions adapted for use over a range of potentially variable conditions, but is generally inadaptable for accurate use outside pre-established parameters. For instance, an embodiment may be "hard-wired" to conduct analysis of the same two sub-ranges in each or either of the short-side and long-side wavelength sets and be programmed to render fixed decisions as to relative motion based on, for example, whether the second ratio is larger or smaller than the first ratio. In other words, the designers and fabricators of such an embodiment operate under a pre-contrived set of atmospheric conditions under which the "hard-wired" decisions rendered by the system are true to a predetermined probability. For instance, a fixed condition that the second ratio is greater than the first ratio corresponds to motion away from the sensor may be valid as long as the first sub-range is set to be 4.50 µm to 4.60 µm and the second sub-range is set to be 4.66 µm to 4.75 µm and as long as the system is used at altitudes of between 0 km and 10 km, the temperature is between 20° F. and 85° F. and the humidity is between 15% and 70% to analyze an emitting source that is within 15 km of the sensor, by way of very specific, non-limiting illustrative example. In other words, such an embodiment depends on the practical optimization of a number of factors in order to have broad applicability with accuracy decreasing as actual atmospheric conditions deviate from the design parameters.

Alternative implementations include steps for factoring measured atmospheric conditions into a ratio-comparative analysis in order to improve accuracy and render the system by which the method is implemented adaptable to a greater variety of atmospheric conditions. In addition to some or all of the aforementioned method steps, alternative implementations further include a step of maintaining an atmospheric-absorption-profile data set including spectral data indicative of plural (at least two) pre-contrived model atmospheres, each of which model atmospheres associates a predetermined set of atmospheric conditions with a corresponding model absorption spectrum from which an expected ratio-comparative behavior as a function of transmission distance is ascertainable for a selected set of sub-ranges included within the model absorption spectrum. Such an implementation further enables the measuring of actual atmospheric conditions for which there exist modeled counterparts associated with the model atmospheres and the storage in computer memory of a measured-conditions data set indicative of the measured conditions in association with data indicative of first and second registered spectral signatures. The maintained atmospheric-absorption-profile data set is then consulted and the data indicative of the model atmosphere that most closely corresponds to the data in the measured-conditions data set is selected and utilized as a reference in the ratio-comparative analysis of the first and second registered spectral signatures. For instance, as previously discussed, the spectral analysis algorithm selects for analysis first and second energy sub-ranges within first and second data sets indicative of first and second spectral signatures as registered at the spectral sensor within each of which sub-ranges it assigns a relative energy value at each of first and second times in order to compute first and second ratios. In order to inform the analysis of whether, for example, the first ratio's being greater than the second ratio corresponds to (i) an increase or (ii) a decrease in distance, reference is made to the "best fit" model atmosphere to ascertain the degree to which energy in each of the corresponding first and second sub-ranges in the model is attenuated as a function of transmission distance and, whether, for instance, in the model atmosphere the first ratio's being greater than the second ratio corresponds to (i) an increase or (ii) a decrease in distance.

Representative embodiments are more completely described in the following detailed description, the elucidation of which is facilitated by the schematic representations of, and numerical and graphical data relating to, an illustrative embodiment contained in the accompanying drawings.

DETAILED DESCRIPTION

The following description of a method and associated apparatus for determining the relative direction of change in distance between an electromagnetic-energy emitting source and a predetermined location (e.g., a spectral sensor) within a predetermined atmosphere is illustrative in nature and is therefore not intended to limit the scope of the invention or its application of uses.

Figure 1:
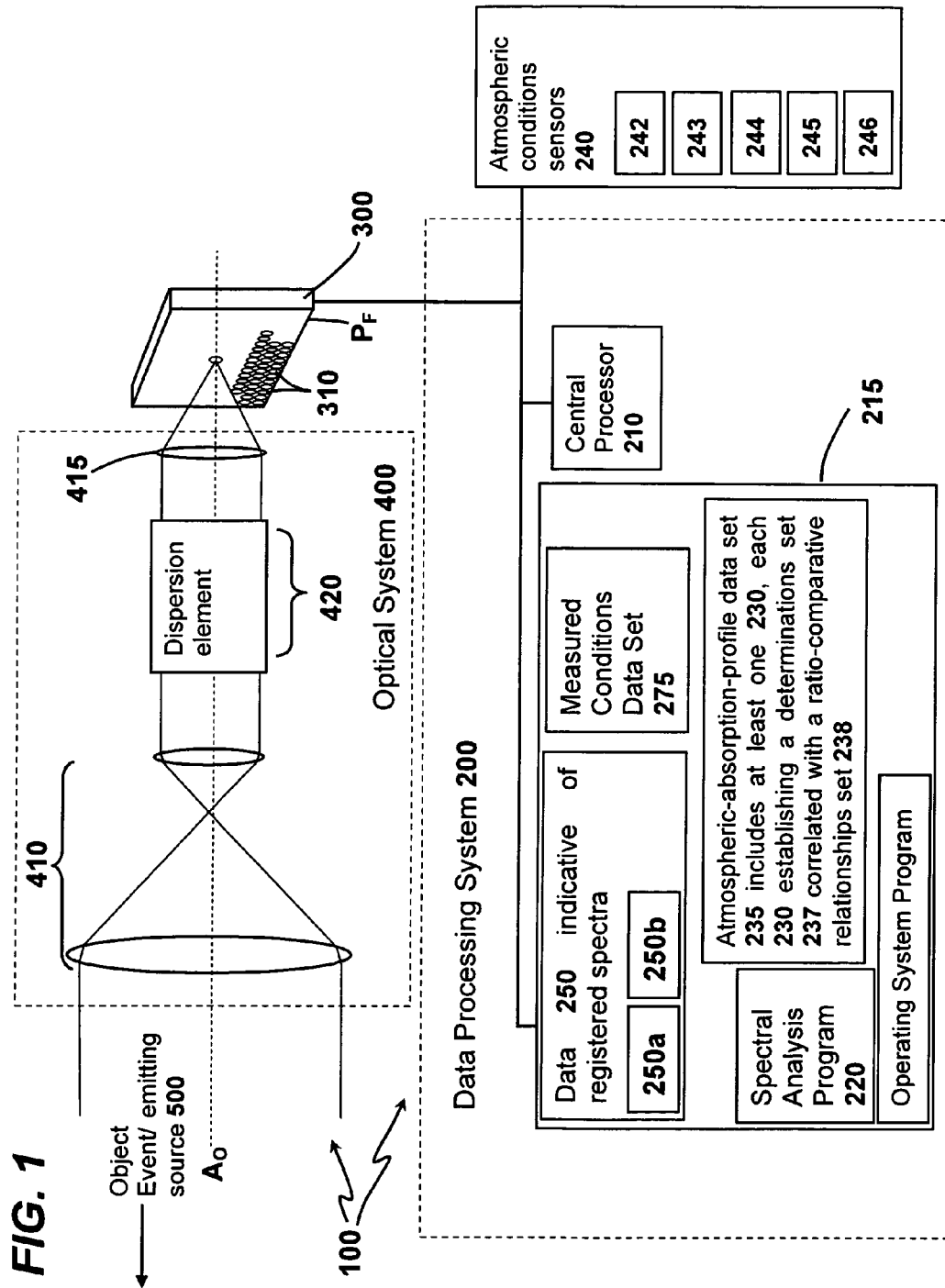
FIG. 1 schematically depicts the architecture of an illustrative system for the passive detection of relative motion between a spectral imager and an electromagnetic-energy emitting source (i.e., an object or event) within a predetermined atmosphere.

Referring to FIG. 1, the architecture of an illustrative spectral analysis system 100 is schematically represented and includes (i) a data processing system 200; (ii) a spectral sensor 300 in the form of an imaging-sensor array 310 communicatively linked to the data processing system 200 and (iii) an optical system 400 adapted for imaging electromagnetic energy emitted from an electromagnetic-energy emitting source 500 (hereinafter "energy source," "emitting source" or "source" 500) external to the optical system 400 onto the spectral sensor 300.

The data processing system 200 includes a central processor 210 and a memory device 215 and is programmed to execute spectral analysis algorithms 220 as described in more detail further in this description. Alternative implementations incorporate any of a variety of conventional imaging sensor arrays 310 adapted to detect wavelengths over a predetermined range of electromagnetic wavelengths and known to those in the relevant technical disciplines.

The optical system 400 schematically represented in the illustrative implementation of FIG. 1 includes a telescope 410 optically aligned with a set of optical dispersion apparatus 420 which may include one or more optically dispersive elements, for example. Located between the set of optical dispersion apparatus 420 and the spectral sensor 300 is a lens 415 situated such that the spectral sensor 300 corresponds in location to the focal plane $P_F$ of the lens 415. It is to be understood that numerous, alternatively configured optical systems 400 may be implemented in order to register spectral signatures at the spectral sensor 300 and that the particular optics chosen are immaterial, in a general sense, to various implementations. However, by way of non-limiting example, the set of optical dispersion apparatus 420 may alternatively include one or more of (i) a prism, (ii) a grism, and (iii) a grating. In one alternative embodiment, the optical dispersion apparatus 420 includes plural lenses, each of which lenses includes an optical filter that passes only wavelengths of interest corresponding to a wavelength sub-region of interest. These lenses (not shown) would not be serially arranged in the optical train; they may, for instance, be arranged side-by-side.

Figure 2:
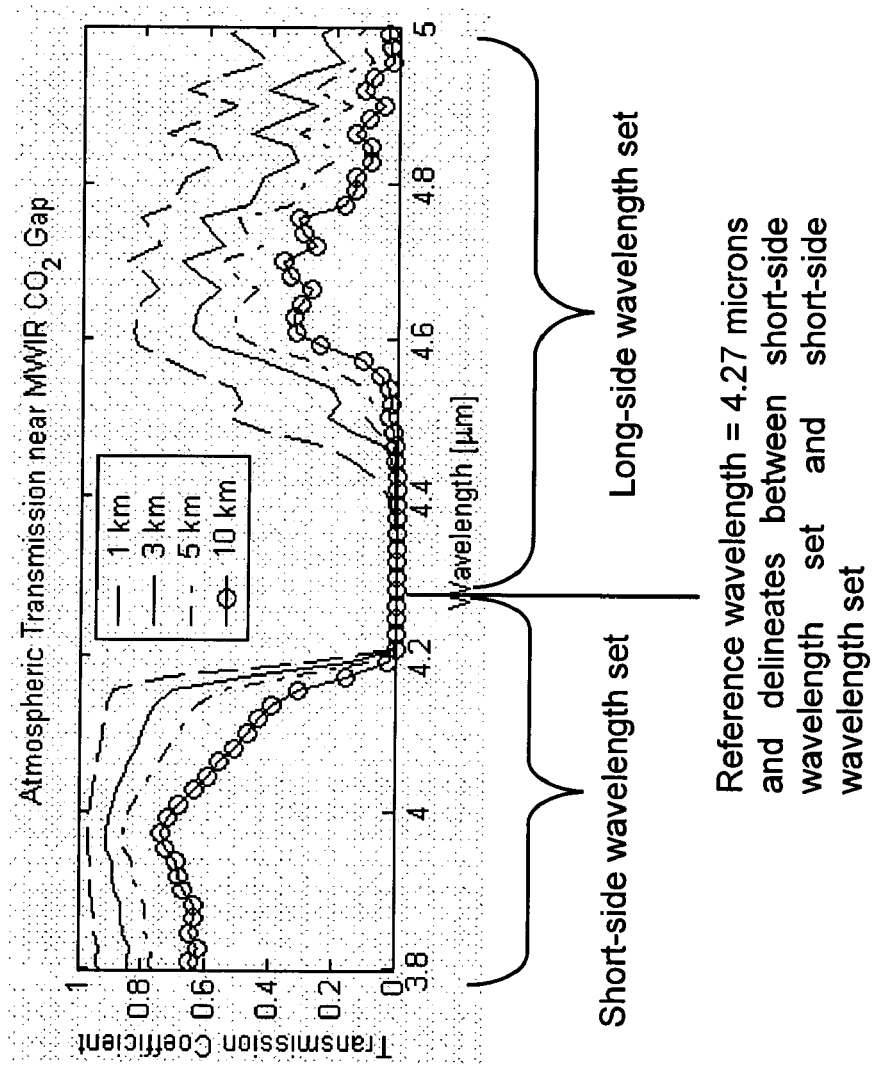
FIG. 2 is a graphical representation of absorption spectra about a reference "dark line" as a function of range in a predetermined atmosphere.
Figure 3:
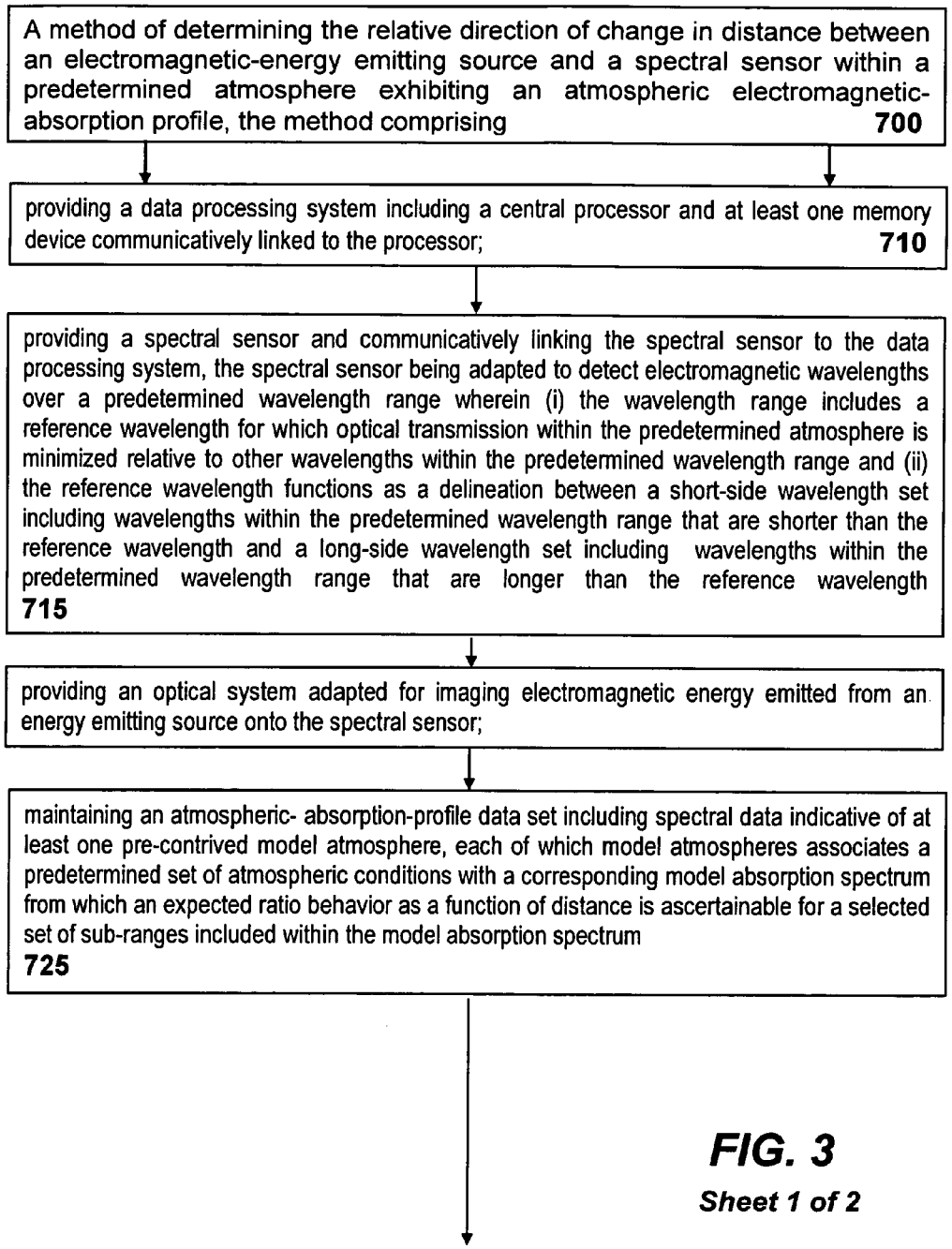
FIG. 3 depicts steps in an illustrative method for determining the relative direction of change in distance between an electromagnetic-energy emitting source and a spectral sensor within a predetermined atmosphere.
Figure 3:
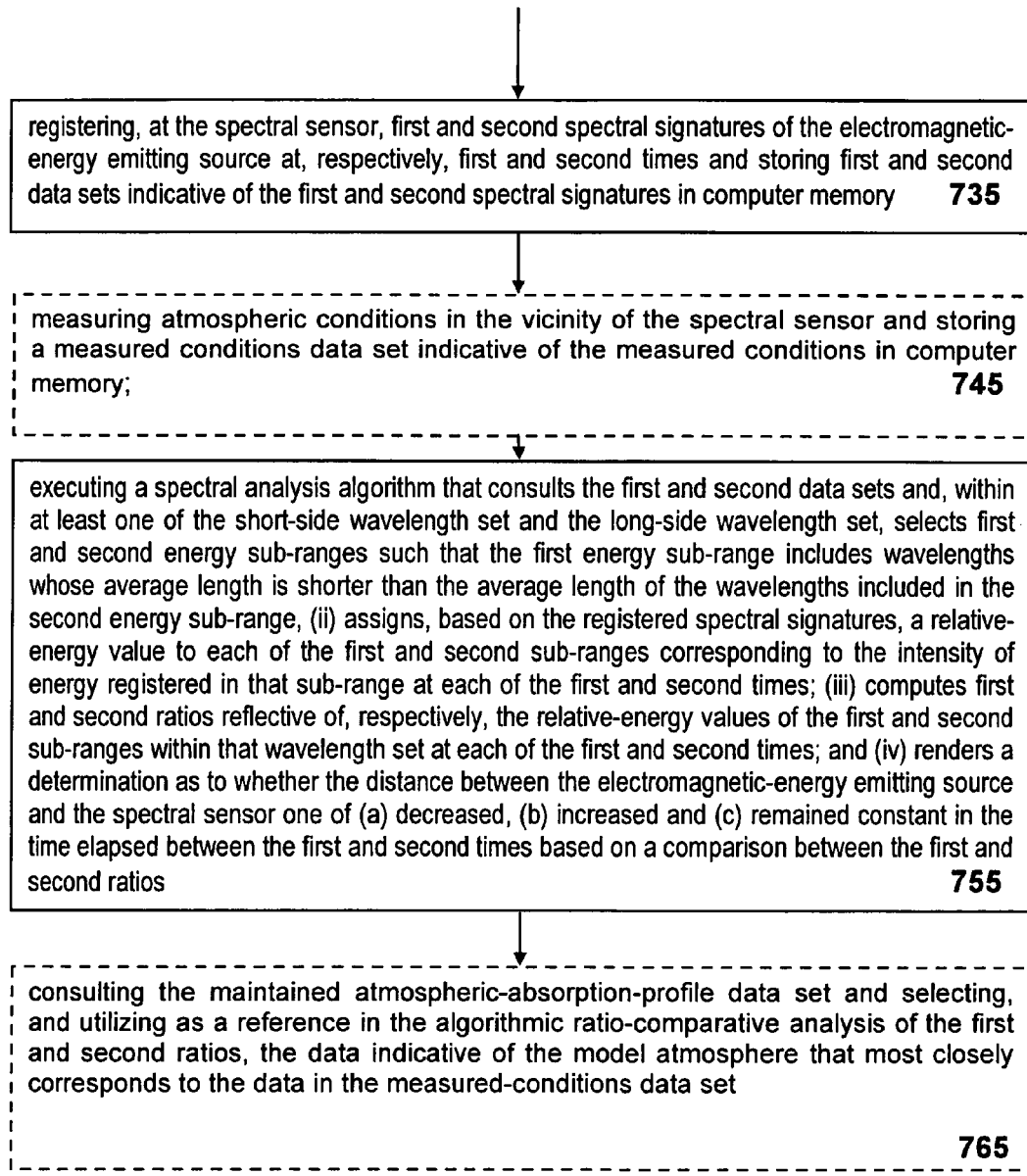

In conjunction with FIGS. 1 through 3, an illustrative method of determining the relative direction of change in distance between an electromagnetic-energy emitting source and a spectral sensor within a predetermined atmosphere exhibiting an atmospheric electromagnetic-absorption profile is described below. Referring to FIG. 3, a sequence of method steps illustrates a method of determining the relative direction of change in distance between an electromagnetic-energy emitting source and a spectral sensor within a predetermined atmosphere. It should be noted that the sequence of steps presented in the drawing and the text to follow is illustrative only and not necessarily indicative of the order in which the steps must be performed. Accordingly, nothing in the drawings, this description or the corresponding claims should be construed so as to limit the scope of the invention to a particular sequence of steps in the absence of explicit statements to the contrary or unless a particular order is inextricably dictated by context (e.g., an instance in which it is impossible to perform a particular step prior to the performance of another step). In addition, various alternative methods may not include all steps depicted. Moreover, although the particular apparatus used to execute method aspects is not relevant, reference is made to the illustrative apparatus of FIG. 1 in order to facilitate comprehension of the illustrative method.

Figure 2A:
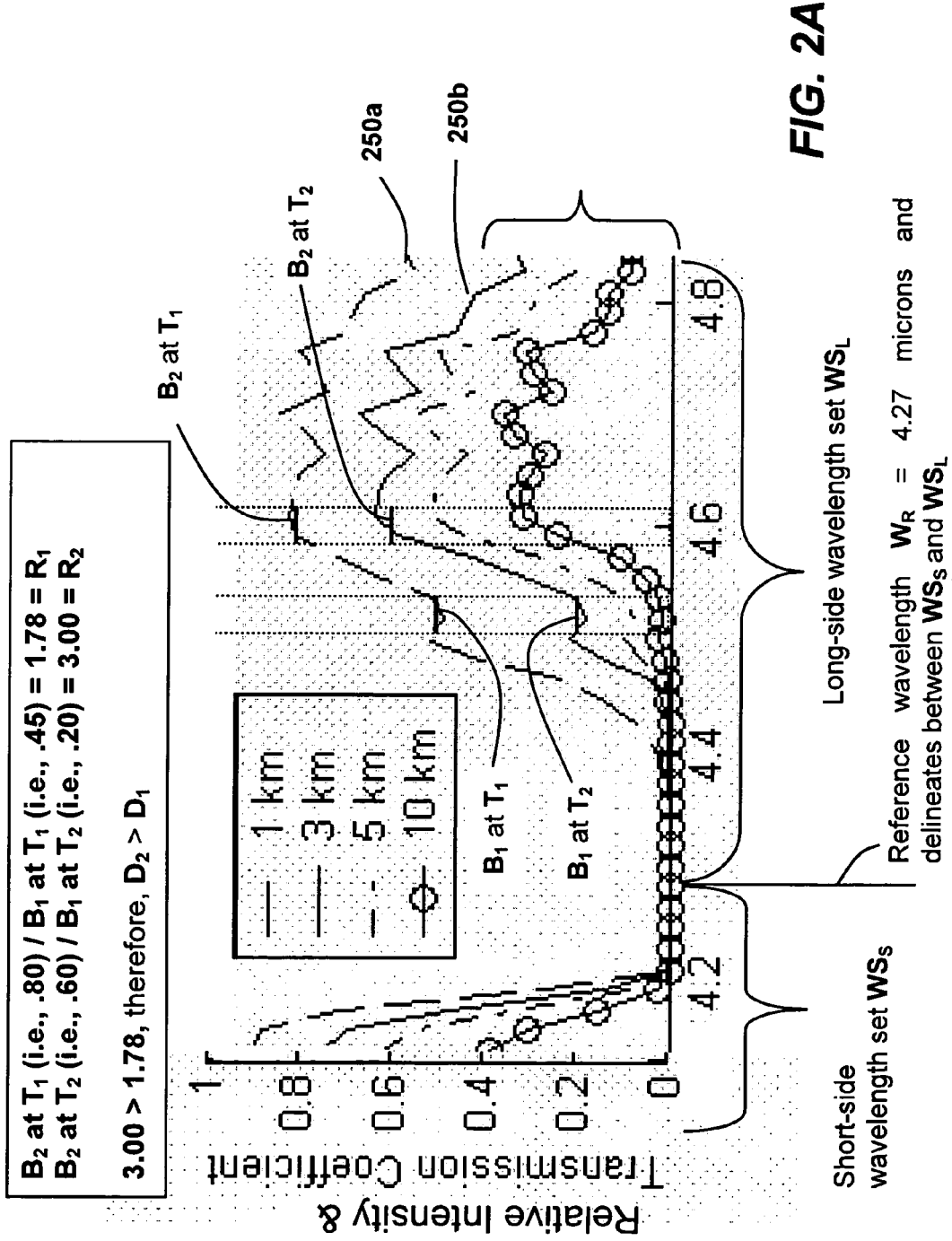
FIG. 2A is a graphical representation of spectral data acquired from an energy emitting source at first and second times.

As described previously in the background and summary, gases, particulates and water vapor present in an environment affect the transmission of electromagnetic energy through that environment. As a general observation, as distance from an energy emitting source is increased, the transmission of energy emitted from that source is decreased for any given wavelength in the emitted spectrum due to absorption and scattering, for example. An atmosphere's electromagnetic-absorption profile is represented, for example, by an absorption spectrum in which a decrease in intensity of radiation at specific wavelengths or ranges of wavelengths characteristic of one or more absorbing substances in the atmosphere is manifested as a pattern of dark lines or bands. FIGS. 2 and 2A are graphical depictions of atmospheric transmission for a particular set of atmospheric conditions (e.g., humidity, temperature, altitude and pressure) near the aforementioned carbon dioxide absorption band in the vicinity of 4.27 µm (i.e., the $CO_2$ gap) for various transmission distances between an emitting source and a point of detection. It will be appreciated from FIGS. 2 and 2A that, as a general trend, as distance increases, transmission decreases. However, in moving from one distance to another, the degree to which transmission is affected varies among wavelengths or ranges of wavelengths; that is, the degree to which the measured intensity of one wavelength is attenuated as a function of distance differs from the degree to which the intensities of other wavelengths are attenuated as a function of transmission distance. For example, consider in FIG. 2A a first band $B_1$ including the wavelengths from between about 4.51 µm and 4.54 µm and a second band $B_2$ including wavelengths from about 4.59 µm to 4.61 µm. The transmission (or energy intensity) in the first band $B_1$ drops more dramatically in moving from 1 km to 3 km than does the transmission of energy in the second band $B_2$. A mathematical way of expressing this observation is that the ratio of energy intensity in the second band $B_2$ at 1 km to energy intensity in the first band $B_1$ at 1 km is less than the ratio of energy intensity in the second band $B_2$ at 3 km to energy intensity in the first band $B_1$ at 3 km. If readings of intensity in the two bands $B_1$ and $B_2$ are registered at first and second times $T_1$ and $T_2$ corresponding respectively, for example, to a first distance $D_1$ of 1 km and a second distance $D_2$ of 3 km, then the conclusion can be drawn, for the example shown, that distance from the emitting source has increased in the time interval $T_2-T_1$. That is, if $B_2(T_1)/B_1(T_1)<B_2(T_2)/B_1(T_1)$, then $D_2>D_1$. As discussed in the summary, alternative implementations utilize the spectral absorption characteristics of a known (e.g., model) atmosphere as a reference for spectral data acquired under live conditions in order to inform the analysis of the acquired data and render determinations as to increased or decreased distance based on the ratio-comparative relationships between the spectral data in the bands selected for analysis as actually acquired and the expected behavior of the relationships among the selected bands under a predetermined set of atmospheric conditions "closest matched" to the actual conditions in which the actual data is acquired.

The illustrative method 700 presented in FIG. 3 includes a step 710 of providing a data processing system 200 including a central processor 210 and at least one memory device 215 communicatively linked to the processor.

At 715, a spectral sensor 300 adapted to detect wavelengths over a predetermined range of electromagnetic wavelengths in provided. The spectral sensor 300 is communicatively linked to the data processing system 200 in an operative manner that facilitates processing by the data processing system 200 of spectral data registered at the spectral sensor 300. An optical system 400 adapted for imaging electromagnetic energy emitted from an energy emitting source 500 onto the spectral sensor 300 is provided at step 720.

Figure 2B:
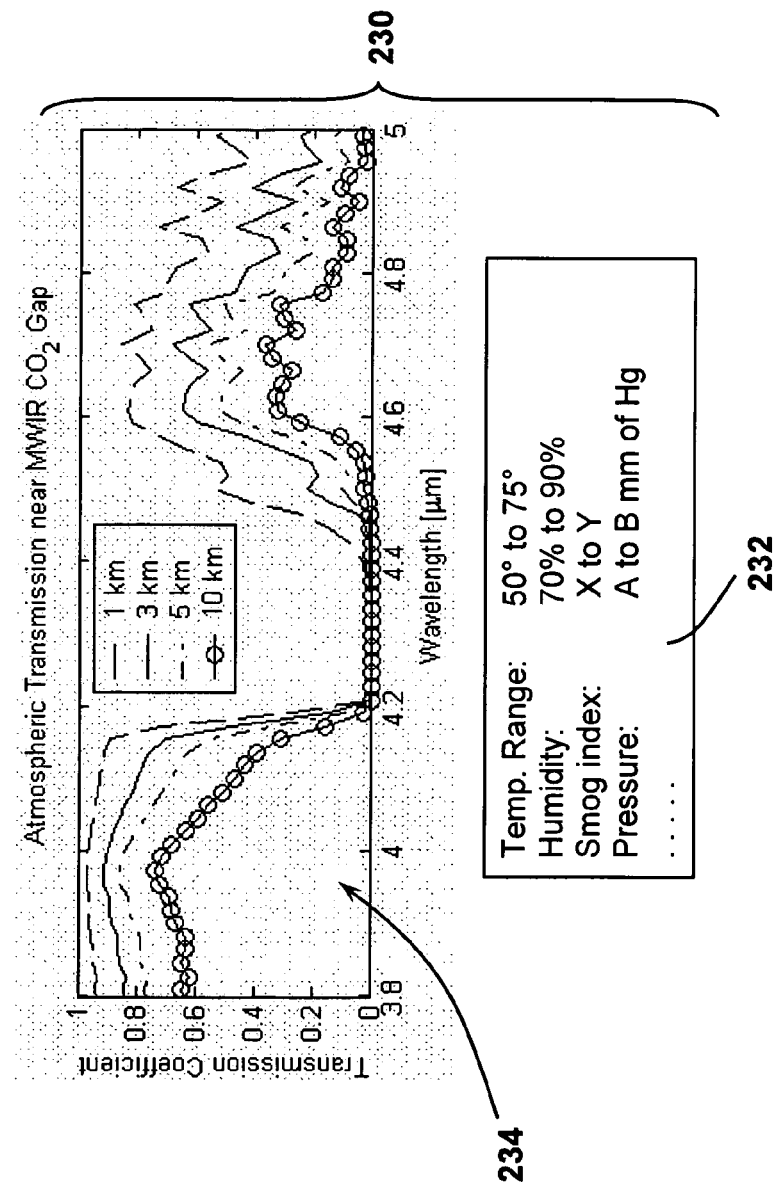
FIG. 2B is a graphical depiction of a portion of the spectral data associated with an atmospheric-absorption-profile data set including spectral data indicative of pre-contrived model atmospheres.

Step 725 indicates the maintenance (e.g., in computer memory 215) of an atmospheric-absorption-profile data set 235 (FIG. 2B) including spectral data indicative of at least one pre-contrived model atmosphere 230, each of which at least one model atmospheres associates a predetermined set of atmospheric conditions 232 with a corresponding model absorption spectrum 234 from which an expected ratio-comparative behavior as a function of transmission distance is ascertainable for a selected set of wavelength sub-ranges included within the model absorption spectrum 234. FIG. 2B graphically represents data in a pre-stored atmospheric-absorption-profile data set 235 including data indicative of pre-contrived model atmosphere 230 associated with a pre-determined set of atmospheric conditions 232. By providing information from which an expected ratio-comparative behavior as a function of distance is ascertainable for a selected set of wavelength sub-ranges, the data indicative of each pre-contrived model atmosphere in the atmospheric-absorption-profile data set 235 establishes, in association with selected first and second energy sub-ranges a determinations set 237 and a ratio-comparative relationships set 238, as noted in FIG. 1. As discussed in the summary, a determinations set 237 includes at least one of (a) a determination that the distance between the electromagnetic-energy emitting source and the predetermined location increased, (b) a determination that the distance between the electromagnetic-energy emitting source and the predetermined location remained unchanged and (c) a determination that the distance between the electromagnetic-energy emitting source and the predetermined location decreased. A ratio-comparative relationships set 238 includes at least one of (a) an indication that the first ratio is greater in magnitude than the second ratio, (b) an indication that the first ratio is equal in magnitude to the second ratio and (c) an indication that the first ratio is lesser in magnitude than the second ratio. Determinations from the determinations set are correlated with indications from the ratio-comparative relationships set. For instance, (i) the determination that the distance between the electromagnetic-energy emitting source and the predetermined location remained unchanged is correlated to the indication that the first ratio is equal in magnitude to the second ratio; (ii) the determination that the distance between the electromagnetic-energy emitting source and the predetermined location increased is correlated with one of (a) the indication that the first ratio is greater in magnitude than the second ratio and (b) the indication that the first ratio is lesser in magnitude than the second ratio; and (iii) the determination that the distance between the electromagnetic-energy emitting source and the predetermined location decreased is correlated with the other of (a) the indication that the first ratio is greater in magnitude than the second ratio and (b) the indication that the first ratio is lesser in magnitude than the second ratio.

Step 735 prescribes registering, at the spectral sensor 300, first and second spectral signatures of the electromagnetic-energy emitting source 500 at, respectively, first and second times T1 and T2 and storing first and second data sets 250$a$ and 250$b$ indicative of the first and second spectral signatures in computer memory 215. FIG. 2 includes graphical representations of first and second sets 250$a$ and 250$b$.

At step 745, actual atmospheric conditions in the vicinity of the spectral sensor 300 are measured and a measured-conditions data set 275 indicative of the measured conditions is stored in computer memory 215. The measured conditions, in various implementations, correspond to those factored into at least one model atmosphere 230 and include, by way of non-limiting example, one or more of (i) temperature, (ii) humidity, (iii) smog (suspended-particulate) content, (iv) pressure and (v) altitude. Implementations accounting for actual atmospheric conditions are discussed in more detail in subsequent paragraphs of this detailed description.

At step 755, a spectral analysis algorithm (program 220, FIG. 1) is executed by the data processing system 200. The first and second data sets 250$a$ and 250$b$ are consulted for the algorithmic analysis of at least first and second selected energy sub-ranges $B_1$ and $B_2$ within at least one of the short-side wavelength set and the long-side wavelength set $WS_S$ and $WS_L$. FIG. 2A graphically illustrates first and second selected energy sub-ranges $B_1$ and $B_2$ within a long-side wavelength set $WS_L$ to the long-side of the reference wavelength $W_R$ of 4.27 μm. Referring still to FIG. 2A, relative-energy values—represented by horizontal lines within the first and second selected energy sub-ranges $B_1$ and $B_2$—corresponding to intensity of energy (e.g. average intensity) registered at first and second times $T_1$ and $T_2$ are assigned to each of the first and second selected energy sub-ranges $B_1$ and $B_2$. First and second ratios $R_1$ and $R_2$ are then computed, wherein an illustrative first ratio $R_1$ relates the energy value assigned to the second sub-range $B_2$ at the first time $T_1$ to the energy value assigned to the first sub-range $B_1$ at the first time $T_1$ and, wherein, an illustrative second ratio $R_2$ relates the energy value assigned to the second sub-range $B_2$ at the second time $T_2$ to the energy value assigned to the first sub-range $B_1$ at the second time $T_2$. Although the illustrative example of FIG. 2A shows the energy values of the second sub-range $B_2$ as numerators and the energy values assigned to the first energy sub-range $B_1$ as denominators, it will be appreciated that this is for illustrative purposes only and that, for example, the numerators and denominators could be reversed; the important aspect being that consistency is maintained in establishing the first and second ratios $R_1$ and $R_2$ in making calculations and comparisons associated therewith. Moreover, any alternative selected ratios that represent equivalent mathematical and conceptual "truths" with respect to the registered data are to be regarded as literally the same expression and, therefore, within the literal scope of the claims. For instance, because the measured energy values are positive, stating that $B_2(T_1)/B_1(T_1)<B_2(T_2)/B_1(T_2)$ corresponds to distance at the second time being greater than the distance at the first time (i.e., $D(T_2)>D(T_1)$ or $D_2>D_1$) is mathematically and conceptually equal to stating that $B_2(T_1)/B_2(T_2)<B_1(T_1)/B_1(T_2)$ corresponds to $D_2>D_1$. In any event, regardless of how the first and second ratios $R_1$ and $R_2$ are defined and calculated in any particular implementation, a comparison between the first and second selected ratios $R_1$ and $R_2$ serves as the basis for rendering a determination as to whether the distance between the emitting source 500 and the spectral sensor 300 one of (a) decreased, (b) increased and (c) remained constant in the time elapsed between the first and second times $T_1$ and $T_2$.

As discussed at some length in the summary, some implementations are designed for use with reference to the absorption spectrum associated with a single and invariable pre-contrived set of atmospheric conditions. However, as described above, alternative implementations wherein an atmospheric-absorption-profile data set 235 including spectral data indicative of pre-contrived model atmospheres 230 is maintained, for example, and wherein a set of atmospheric-condition sensors 240 is provided for measuring atmospheric conditions include additional steps for rendering the spectral analysis system 100 adaptable for use under a greater variety of conditions. Illustrative, non-limiting examples of atmospheric-condition sensors 240 variably associated with alternative implementations include, as shown in FIG. 1, (i) a temperature sensor 242, (ii) a humidity sensor 243, (iii) a pressure sensor 244, (iv) an altimeter 245 and (v) a nephelometer 246, or other instrument, for measuring the gaseous and suspended-particulate (aerosol) characteristics of the relevant atmosphere. Atmospheric data registered by at least one atmospheric-conditions sensor 240 is stored as, or in association with, a registered (or measured) conditions data set 275. With reference to FIG. 3, at step 765, the maintained atmospheric-absorption-profile data set 235 is consulted and the data indicative of the model atmosphere 230 that most closely corresponds to the data in the measured-conditions data set 275 is selected and utilized as a reference in the algorithmic ratio-comparative analysis of the computed first and second ratios $R_1$ and $R_2$. For example, if, with respect to the registered spectra, $R_1=B_2(T_1)/B_1(T_1)$; $R_2=B_2(T_2)/B_1(T_2)$; and $R_2>R_1$ and, for first and second sub-ranges in the model absorption spectrum 234 corresponding to the first and second sub-ranges $B_1$ and $B_2$ from which the ratios $R_1$ and $R_2$ were computed, the model atmosphere 230 indicates that the condition that $R_2>R_1$ corresponds to an increase in distance, then the algorithm renders a determination that distance increased between the first and second times $T_1$ and $T_2$.

The foregoing is considered to be illustrative of the principles of the invention. Furthermore, since modifications and changes to various aspects and implementations will occur to those skilled in the art without departing from the scope and spirit of the invention, it is to be understood that the foregoing does not limit the invention as expressed in the appended claims to the exact construction, implementations and versions shown and described.

What is claimed is:

1. A method of determining, within a predetermined atmosphere exhibiting an atmospheric electromagnetic-absorption profile, a relative direction of change in distance between an electromagnetic-energy emitting source and a predetermined location, the method comprising:

providing reference-profile data indicative of an electromagnetic-absorption profile associated with a model atmosphere and including indications as to the absorption behavior, within the model atmosphere, of each wavelength of a selected set of wavelengths as a function of transmission distance;

selecting a wavelength range within which to measure the relative intensity of detectable energy emitted from the emitting source, the selected wavelength range including wavelengths for which absorption behavior as a function of transmission distance is represented in the reference-profile data;

selecting from within the wavelength range first and second energy sub-ranges such that (i) the first energy sub-range includes wavelengths whose average length is shorter than the average length of the wavelengths included in the second energy sub-range, (ii) the average wavelength within the first energy sub-range and the average wavelength within the second energy sub-range are disparately absorbed as a function of transmission distance in the predetermined atmosphere and (iii) each of the first and second sub-ranges includes at least one wavelength for which absorption behavior as a function of transmission distance is represented in the reference-profile data;

measuring, from the predetermined location at each of first and second times, the relative intensity of detectable energy emitted from the emitting source within each of the first and second energy sub-ranges and associating relative-energy values to each of the first and second sub-ranges, each relative-energy value associated with one of the first and second sub-ranges corresponding to the intensity of energy detected in that sub-range at one of the first and second times;

computing first and second ratios comparatively indicative of the intensity of energy detected, as represented by the assigned relative-energy values, within the first and second sub-ranges at each of the first and second times; and rendering, with reference to the reference-profile data, a determination as to whether the distance between the electromagnetic-energy emitting source and the predetermined location one of (a) decreased, (b) increased and (c) remained constant in the time elapsed between the first and second times based on a comparison between the first and second ratios.

2. The method of claim 1 further comprising establishing in association with the reference-profile data and the selected first and second energy sub-ranges (i) a determinations set including at least one of (a) a determination that the distance between the electromagnetic-energy emitting source and the predetermined location increased, (b) a determination that the distance between the electromagnetic-energy emitting source and the predetermined location remained unchanged and (c) a determination that the distance between the electromagnetic-energy emitting source and the predetermined location decreased and (ii) a ratio-comparative relationships set including at least one of (a) an indication that the first ratio is greater in magnitude than the second ratio, (b) an indication that the first ratio is equal in magnitude to the second ratio and (c) an indication that the first ratio is lesser in magnitude than the second ratio.

3. The method of claim 2 wherein, (i) the determination that the distance between the electromagnetic-energy emitting source and the predetermined location remained unchanged is correlated to the indication that the first ratio is equal in magnitude to the second ratio;

(ii) the determination that the distance between the electromagnetic-energy emitting source and the predetermined location increased is correlated with one of (a) the indication that the first ratio is greater in magnitude than the second ratio and (b) the indication that the first ratio is lesser in magnitude than the second ratio; and (iii) the determination that the distance between the electromagnetic-energy emitting source and the predetermined location decreased is correlated with the other of (a) the indication that the first ratio is greater in magnitude than the second ratio and (b) the indication that the first ratio is lesser in magnitude than the second ratio.

4. The method of claim 1 wherein (i) the reference-profile data include data indicative of plural disparate electromagnetic-absorption profiles, each of which profiles is associated with a model atmosphere and includes indications as to the absorption behavior, within the model atmosphere with which that profile is associated, of each wavelength of a selected set of wavelengths as a function of transmission distance and (ii) each profile is formulated on the basis of an assigned set of values for each atmospheric condition of a selected set of atmospheric conditions.

5. The method of claim 4 wherein the set of atmospheric conditions comprises at least one of (i) temperature, (ii) humidity, (iii) suspended-particulate content, (iv) pressure and (v) altitude.

6. The method of claim 4 further comprising the steps of (a) measuring a value of at least one atmospheric condition in the pre-determined atmosphere within which a determination as to change in distance between the emitting source and the predetermined location is to be rendered; and (b) selecting from the reference-profile data, as an analytical reference, the electromagnetic-absorption profile formulated on the basis of assigned set values corresponding most closely, relative to other profiles within the reference-profile data, to the at least one measured atmospheric-condition as a basis for rendering a determination as to whether the distance between the electromagnetic-energy emitting source and the predetermined location one of (a) decreased, (b) increased and (c) remained constant in the time elapsed between the first and second times based on a comparison between the first and second ratios.

7. The method of claim 1 wherein the wavelength range within which to measure the relative intensity of detectable energy emitted from the emitting source is selected with reference to a reference wavelength for which optical transmission within the predetermined atmosphere is minimized relative to wavelengths within the selected wavelength range.

8. The method of claim 7 wherein (i) the reference wavelength is included within the selected wavelength range and functions as a delineation between a short-side wavelength set including wavelengths within the selected wavelength range that are shorter than the reference wavelength and a long-side wavelength set including wavelengths within the selected wavelength range that are longer than the reference wavelength and (ii) the first and second energy sub-ranges associated with any particular ratio-comparative analysis are selected from the same one of the short-side wavelength set and the long-side wavelength set.

9. The method of claim 7 wherein the reference wavelength is a wavelength at which the carbon dioxide absorption band of earth's atmosphere is manifest.

10. A method of determining the relative direction of change in distance between an electromagnetic-energy emitting source and a spectral sensor within a predetermined atmosphere exhibiting an atmospheric electromagnetic-absorption profile, the method comprising:
providing a data processing system including a central processor and at least one memory device communicatively linked to the processor;
providing a spectral sensor and communicatively linking the spectral sensor to the data processing system, the spectral sensor being adapted to detect electromagnetic wavelengths over a predetermined wavelength range
registering, at the spectral sensor, first and second spectral signatures of the electromagnetic-energy emitting source at, respectively, first and second times and storing first and second data sets indicative of the first and second spectral signatures in computer memory;
consulting the first and second data sets and selecting first and second energy sub-ranges such that (i) the first energy sub-range includes wavelengths whose average length is shorter than the average length of the wavelengths included in the second energy sub-range and (ii) the average wavelength within the first energy sub-range and the average wavelength within the second energy sub-range are disparately absorbed as a function of transmission distance in the predetermined atmosphere;
assigning, based on the registered spectral signatures, relative-energy values to each of the first and second sub-ranges, each relative-energy value associated with one of the first and second sub-ranges corresponding to the intensity of energy detected in that sub-range at one of the first and second times;
computing first and second ratios comparatively indicative of the intensity of energy detected, as represented by the assigned relative-energy values, within the first and second sub-ranges at each of the first and second times; and
rendering a determination as to whether the distance between the electromagnetic-energy emitting source and the predetermined location one of (a) decreased, (b) increased and (c) remained constant in the time elapsed between the first and second times based on a ratio-comparative analysis including a comparison of the relative magnitudes of the first and second ratios.

11. The method of claim 10 further comprising maintaining an atmospheric-absorption-profile data set including spectral data indicative of at least one electromagnetic-absorption profile associated with at least one pre-contrived model atmosphere and including indications as to the absorption behavior, within the at least one model atmosphere, of each wavelength of a selected set of wavelengths as a function of transmission distance and from which an expected ratio-comparative behavior as a function of transmission distance is ascertainable for a selected set of sub-ranges included within the model atmosphere, wherein the step of rendering a determination as to whether the distance between the electromagnetic-energy emitting source and the predetermined location one of (a) decreased, (b) increased and (c) remained constant is based upon consulting the atmospheric-absorption-profile data set and using the spectral data indicative of at least one electromagnetic-absorption profile associated with at least one model atmosphere as a reference in the ratio-comparative analysis.

12. The method of claim 11 wherein (i) the absorption-profile data set includes data indicative of plural disparate electromagnetic-absorption profiles, each of which profiles is associated with a model atmosphere and includes indications as to the absorption behavior, within the model atmosphere with which that profile is associated, of each wavelength of a selected set of wavelengths as a function of transmission distance and (ii) each profile is formulated on the basis of an assigned set of values for each atmospheric condition of a selected set of atmospheric conditions.

13. The method of claim 12 wherein the set of atmospheric conditions comprises at least one of (i) temperature, (ii) humidity, (iii) suspended-particulate content, (iv) pressure and (v) altitude.

14. The method of claim 12 further comprising the steps of
(a) measuring, in the vicinity of the spectral sensor, a value of at least one atmospheric condition in the pre-determined atmosphere within which a determination as to change in distance between the emitting source and the predetermined location is to be rendered and storing a measured conditions data set indicative of the at least one measured atmospheric condition in computer memory; and
(b) consulting the maintained atmospheric-absorption-profile data set and selecting, as a ratio-comparative analytical reference, the electromagnetic-absorption profile formulated on the basis of assigned set values corresponding most closely, relative to other profiles within the atmospheric-absorption-profile data set, to the data indicated in the measured-conditions data set as a basis for rendering a determination as to whether the distance between the electromagnetic-energy emitting source and the predetermined location one of (a) decreased, (b) increased and (c) remained constant in the time elapsed between the first and second times.

15. The method of claim 14 wherein the set of atmospheric conditions comprises at least one of (i) temperature, (ii) humidity, (iii) suspended-particulate content, (iv) pressure and (v) altitude.

16. The method of claim 10 wherein the wavelength range within which to measure the relative intensity of detectable energy emitted from the emitting source is selected with reference to a reference wavelength for which optical transmission within the predetermined atmosphere is minimized relative to wavelengths within the selected wavelength range.

17. The method of claim 16 wherein the reference wavelength is a wavelength at which the carbon dioxide absorption band of earth's atmosphere is manifest.

* * * * *